United States Patent
Jung et al.

(10) Patent No.: US 7,828,949 B2
(45) Date of Patent: Nov. 9, 2010

(54) BIOMOLECULE DETECTION DEVICE, MOBILE PHONE FOR BIOMOLECULE DETECTION, AND BIOMOLECULE DETECTION METHOD

(75) Inventors: Moon Youn Jung, Daejeon (KR); Se Ho Park, Daejeon (KR); Dong Ho Shin, Daejeon (KR); Hyeon Bong Pyo, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 819 days.

(21) Appl. No.: 11/634,710

(22) Filed: Dec. 6, 2006

(65) Prior Publication Data
US 2007/0131552 A1 Jun. 14, 2007

(30) Foreign Application Priority Data
Dec. 8, 2005 (KR) ............... 10-2005-0120115
Jun. 22, 2006 (KR) ............... 10-2006-0056531

(51) Int. Cl.
*G01N 27/26* (2006.01)

(52) U.S. Cl. ............... 204/456; 204/606; 204/612; 204/451; 204/601; 204/605; 435/6; 435/7.1; 435/287.2

(58) Field of Classification Search ............... 455/73, 455/91, 400, 403; 204/459, 610, 456, 606, 204/450, 451, 466, 601, 605, 612; 600/300, 600/301, 309–310, 316, 322, 347, 365, 481, 600/500, 587, 595; 128/903–904; 702/19, 702/104; 434/235–238, 262; 273/429, 440, 273/459, 148 B; 382/313; 435/6, 7.1, 287.2
See application file for complete search history.

(56) References Cited

U.S. PATENT DOCUMENTS

| | | | | |
|---|---|---|---|---|
| 5,194,133 A | * | 3/1993 | Clark et al. | 204/608 |
| 5,746,901 A | * | 5/1998 | Balch et al. | 204/606 |
| 5,800,993 A | * | 9/1998 | Bhat | 435/6 |
| 6,473,609 B1 | * | 10/2002 | Schwartz et al. | 455/406 |
| 6,699,188 B2 | * | 3/2004 | Wessel | 600/300 |
| 6,871,972 B2 | * | 3/2005 | Ju | 362/26 |
| 2002/0058273 A1 | * | 5/2002 | Shipwash | 435/6 |

(Continued)

FOREIGN PATENT DOCUMENTS

JP 2004-101253 4/2004
KR 1020020011730 2/2002

OTHER PUBLICATIONS

Form B—Proposal Summary, Printed Sep. 19, 2005.*
Nokia 9000 Communicator Specification, pre 2005.*

*Primary Examiner*—Alexa D Neckel
*Assistant Examiner*—Jennifer Dieterle
(74) *Attorney, Agent, or Firm*—Ladas & Parry LLP (57) ABSTRACT

Provided are a biomolecule detection device, a mobile phone for biomolecule detection, and a biomolecule detection method. The biomolecule detection device includes an electrophoresis unit comprising an electrophoretic gel filtering erythrocytes and leukocytes in blood and transferring proteins and DNAs in the blood, and at least one type of a probe biomolecule, immobilized in the electrophoretic gel, reacting with a target biomolecule; a conversion unit converting a result of a reaction between the target biomolecule and the probe biomolecule to an electrical signal; and a lead-out unit receiving, converting, and transmitting the electrical signal.

20 Claims, 8 Drawing Sheets

U.S. PATENT DOCUMENTS

| | | | |
|---|---|---|---|
| 2002/0101197 A1* | 8/2002 | Lys et al. | 315/291 |
| 2002/0182649 A1* | 12/2002 | Weinberger et al. | 435/7.9 |
| 2003/0032077 A1* | 2/2003 | Itoh et al. | 435/14 |
| 2004/0144652 A1* | 7/2004 | Kasai et al. | 204/601 |
| 2004/0197793 A1* | 10/2004 | Hassibi et al. | 435/6 |
| 2005/0208539 A1* | 9/2005 | Vann et al. | 435/6 |
| 2005/0237524 A1* | 10/2005 | Kamei et al. | 356/318 |
| 2005/0255896 A1* | 11/2005 | Ting | 455/575.3 |

* cited by examiner

BIOMOLECULE DETECTION DEVICE, MOBILE PHONE FOR BIOMOLECULE DETECTION, AND BIOMOLECULE DETECTION METHOD

CROSS-REFERENCE TO RELATED PATENT APPLICATION

This application claims priority from Korean Patent Application No. 10-2005-0120115, filed on Dec. 8, 2005, and No. 10-2006-0056531, filed on Jun. 22, 2006, in the Korean Intellectual Property Office, the disclosures of which are incorporated herein in their entireties by reference.

FIELD OF INVENTION

The present invention relates to a biomolecule detection device, a mobile phone for biomolecule detection, and a biomolecule detection method.

DESCRIPTION OF THE RELATED ART

Electrophoresis is a molecular biological assay that separates molecules in a sample based on molecular size and conformation and an isoelectric point by placing a matrix material with a microstructure, such as an agarose or polyacrylamide gel, in an electrolyte buffer solution and generating an electric field between opposite electrodes. Target molecules may be single-molecules such as DNAs, RNAs, or proteins, or if desired, may also be complex molecules such as DNA-protein complexes or DNA-RNA complexes.

Generally, a voltage of fifty to several hundreds or thousands of volts may be applied across opposite ends of an electrophoretic system. However, if an area under the influence of an electric field, i.e., an area of a space where an electrolyte is filled is small, electrophoresis can occur even at a voltage of several volts.

During electrophoresis, a molecular mixture in a sample is separated into its components according to a frictional force between the components and pores of a matrix structure while it migrates toward the bottom of a gel by the flow of an electrolyte solvent and the attraction and repulsion between two opposite electrodes. For example, electrophoretic separation can be performed on the basis of the molecular size or conformation of DNA, the molecular weight or three-dimensional structure of protein, etc.

Recently, two-dimensional (2D) electrophoresis is used to achieve more precise separation of a protein mixture into individual proteins. In 2D electrophoresis, proteins are separated according to their molecular weights (primary separation) followed by their isoelectric points (secondary separation), and thus, it is possible to distribute the proteins in a 2D plane according to each kind of protein. In particular, the 2D electrophoresis is very useful in the identification of disease-associated protein markers and physiological research.

Most protein analyses for diagnostics such as blood typing, pregnancy testing, detection of hepatitis, and immunodetection are based on antigen-antibody interactions. Antigen-antibody interaction-based assays have been widely used in diagnostics due to high specificity, high stability upon lyophilization, application of well-known immobilization techniques, etc.

In antigen-antibody interaction-based assays, a capturing antibody is immobilized on a solid phase, and a fluorescence- or enzyme-linked primary antibody is incubated with a sample. When the sample moves by transfer of a mobile phase, an antigen in the sample is bound to the capturing antibody and concentrated, thereby resulting in color development by a fluorophore or chromophore reagent.

Hitherto, there is no report about a mobile phone that can be used for the diagnostic detection of disease regardless of time and place and for remote medical consultation.

SUMMARY OF THE INVENTION

The present invention provides a biomolecule detection device that can be used for biomolecule detection (e.g., self-diagnosis of disease) regardless of time and place.

The present invention also provides a mobile phone for biomolecule detection that can be used for biomolecule detection (e.g., self-diagnosis of disease) regardless of time and place, and at the same time, can transmit the detection results to a medically trained person (e.g., a doctor) and receive the medical consultation wirelessly.

The present invention also provides a biomolecule detection method capable of performing biomolecule detection (e.g., self-diagnosis of disease) regardless of time and place, and transmitting the detection results to a medically trained person (e.g., a doctor) and receiving the medical consultation wirelessly.

According to an aspect of the present invention, there is provided a biomolecule detection device including: an electrophoresis unit including an electrophoretic gel, and at least one type of a probe biomolecule, immobilized in the electrophoretic gel, reacting with a target biomolecule; a conversion unit converting a result of a reaction between the target biomolecule and the probe biomolecule to an electrical signal; and a lead-out unit receiving, converting, and transmitting the electrical signal.

The electrophoresis unit may further include a filter filtering the sample.

The electrophoresis unit may further include a sample inlet.

The electrophoresis unit may further include an electrode generating an electric field necessary for electrophoresis.

The electrophoresis unit may further include a polymer material which is disposed in the electrophoretic gel and immobilizes the probe biomolecule.

The electrophoresis unit may further include a microchannel including the electrophoretic gel and the probe biomolecule.

The electrophoresis unit may further include a detecting probe biomolecule conjugated with a gold colloid.

The electrophoretic gel may be an agarose gel or a polyacrylamide gel.

The target biomolecule and the probe biomolecule may be each a nucleic acid or a protein.

The nucleic acid may be selected from the group consisting of DNAs, RNAs, PNAs, LNAs, and hybrids thereof.

The protein may be selected from the group consisting of enzymes, substrates, antigens, antibodies, ligands, aptamers, and receptors.

The target biomolecule and the probe biomolecule may be respectively an antigen and an antibody or a target DNA and a probe DNA.

The electrophoresis unit may further include two substrates facing each other, and the electrophoretic gel and the probe biomolecule may be interposed between the two substrates.

The two substrates may be made of a transparent material.

The conversion unit may be a photodiode array.

The photodiode array may be a photodiode array capable of detecting visible light or UV light.

According to another aspect of the present invention, there is provided a mobile phone for biomolecule detection, including: an electrophoresis unit including an electrophoretic gel, and at least one type of a probe biomolecule, immobilized in the electrophoretic gel, reacting with a target biomolecule; a conversion unit converting a result of a reaction between the target biomolecule and the probe biomolecule to an electrical signal; a lead-out unit receiving, converting, and transmitting the electrical signal; a power supply unit supplying power to the electrophoresis unit, the conversion unit, and the lead-out unit; an optical source irradiating light to the electrophoresis unit; and a transmitter transmitting information received from the lead-out unit wirelessly.

The optical source may be an LCD screen of the mobile phone.

The optical source may further include a UV light source.

According to still another aspect of the present invention, there is provided a method of detecting a target biomolecule using a mobile phone for biomolecule detection, the mobile phone including an electrophoresis unit including an electrophoretic gel, and at least one type of a probe biomolecule, immobilized in the electrophoretic gel, reacting with a target biomolecule; a conversion unit converting a result of a reaction between the target biomolecule and the probe biomolecule to an electrical signal; a lead-out unit receiving, converting, and transmitting the electrical signal; a power supply unit supplying power to the electrophoresis unit, the conversion unit, and the lead-out unit; an optical source irradiating light to the electrophoresis unit; and a transmitter transmitting information received from the lead-out unit wirelessly, the method including: loading a sample on the electrophoresis unit to perform electrophoresis; irradiating light to the electrophoresis unit using the optical source; and transmitting the detection result wirelessly.

The method may further include mixing the sample with a solution including a molecule capable of binding with the target biomolecule and absorbing light emitted from the optical source or a molecule capable of binding with the target biomolecule, absorbing light emitted from the optical source, and emitting light with a predetermined wavelength, prior to loading the sample on the electrophoresis unit.

The sample may be selected from the group consisting of saliva, urine, blood, serum, cell culture, and drinking water.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
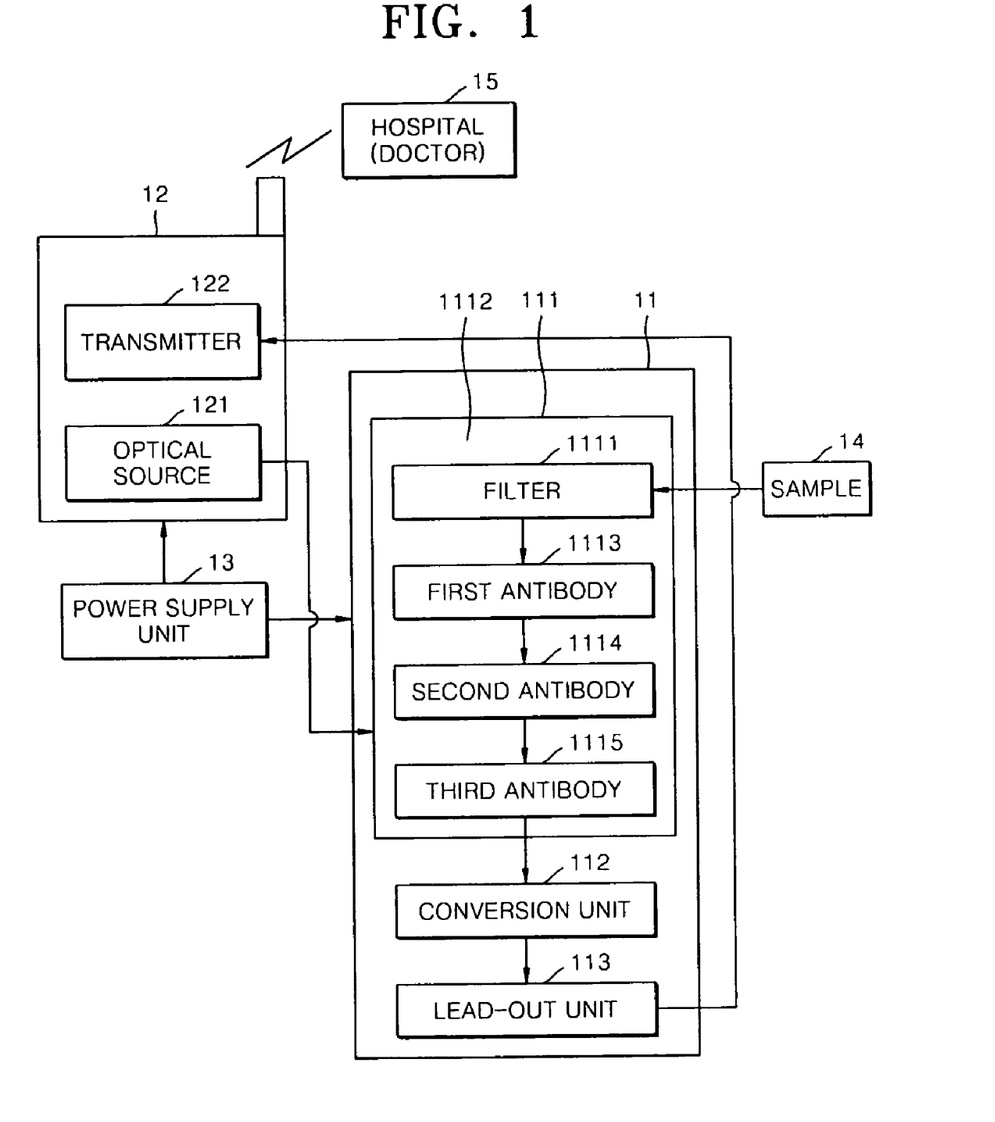
FIG. 1 is a block diagram illustrating a biomolecule detection device according to an embodiment of the present invention and a mobile phone for biomolecule detection including the device.

FIG. 1 is a block diagram illustrating a biomolecule detection device according to an embodiment of the present invention and a mobile phone for biomolecule detection including the device.

Referring to FIG. 1, a mobile phone for biomolecule detection includes a biomolecule detection device 11, a mobile phone body 12, and a power supply unit 13.

The biomolecule detection device 11 includes an electrophoresis unit 111, a conversion unit 112, and a lead-out unit 113. The electrophoresis unit 111 includes a filter 1111 for filtering a sample 14 introduced through a sample inlet (not shown), an electrophoretic gel 1112, and first, second, and third antibodies 1113, 1114, and 1115, immobilized on the electrophoretic gel 1112, reacting with specific antigens.

The electrophoretic gel 1112 is used for two purposes: (1) for filtering blood cells (erythrocytes and leukocytes) in blood by adjusting a pore size of the gel 1112 to detect marker proteins or DNAs in the blood and (2) for use as a transfer medium of proteins or DNAs in an electric field.

The conversion unit 112 converts antigen-antibody interaction results to electrical signals. The conversion unit 112 may be a photodiode array, and the photodiode array may be a photodiode array capable of detecting visible/UV light. The lead-out unit 113 receives the electrical signals from the conversion unit 112 and converts and transmits the received signals.

The mobile phone body 12 includes an optical source 121 and a transmitter 122. The optical source 121 irradiates light to the electrophoresis unit 111. An LCD screen equipped in the mobile phone body 12 may be used as the optical source 121. In addition to the LCD screen, a UV light source may be further used. The transmitter 122 receives information from the lead-out unit 113 and transmits the received information to a hospital (or a doctor) 15 wirelessly.

The power supply unit 13 supplies a power to the mobile phone body 12, and the electrophoresis unit 111, the conversion unit 112, and the lead-out unit 113 of the biomolecule detection device 11. A conventional battery that can be installed in the mobile phone body 12 may be used as the power supply unit 13.

In the present invention, a biomolecule may be a nucleic acid or a protein. The nucleic acid may be selected from the group consisting of DNAs, RNAs, PNAs, LNAs, and hybrids thereof, and the protein may be selected from the group consisting of enzymes, substrates, antigens, antibodies, ligands, aptamers, and receptors. In the present invention, a target biomolecule and a probe biomolecule may be respectively an antigen and an antibody or a target DNA and a probe DNA.

Figure 2:
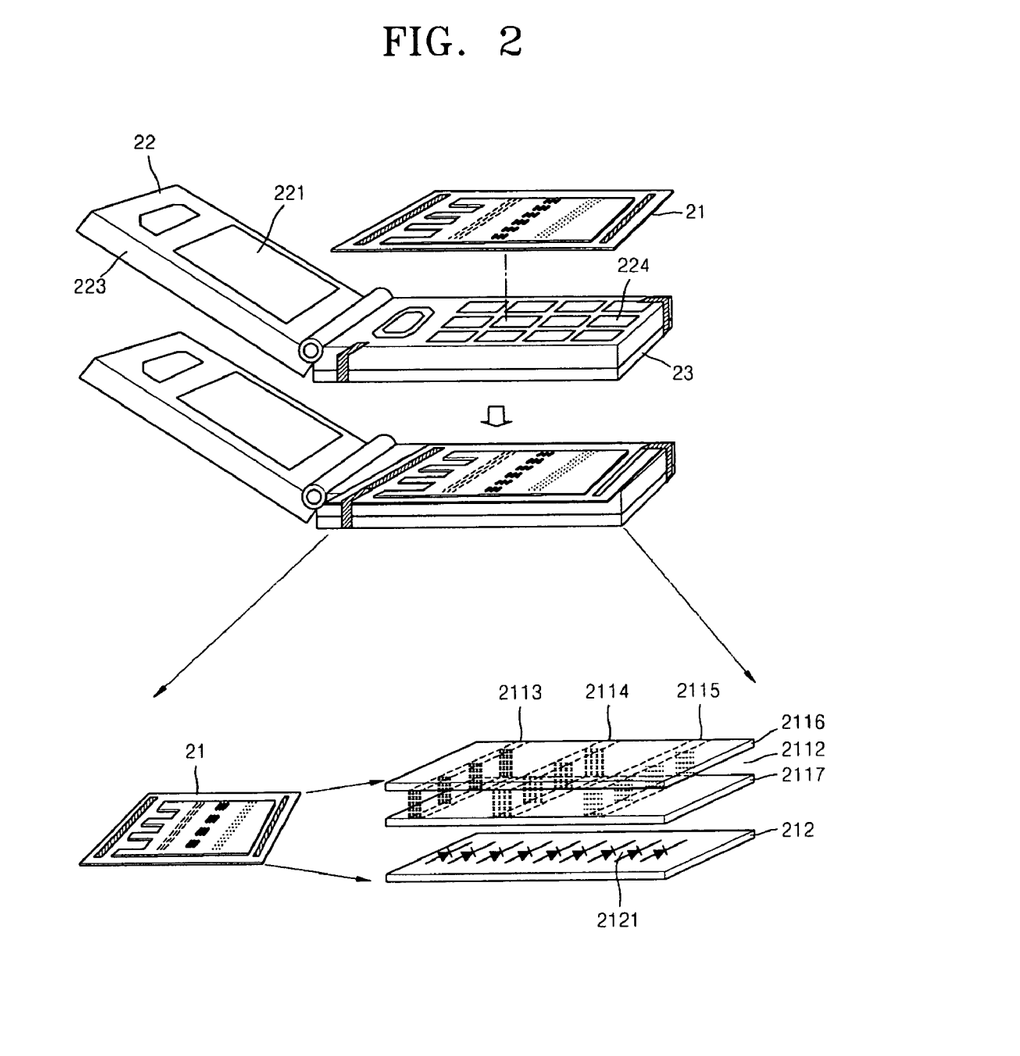
FIG. 2 is an exploded perspective view schematically illustrating a biomolecule detection device according to an embodiment of the present invention and a mobile phone for biomolecule detection including the device.

FIG. 2 is an exploded perspective view schematically illustrating a biomolecule detection device according to an embodiment of the present invention and a mobile phone for biomolecule detection including the device.

Referring to FIG. 2, a mobile phone body 22 includes an LCD screen 221, a cover 223, and a keypad 224 equipped with a battery 23 used as a power supply source. A biomolecule detection chip 21 is attached onto the keypad 224.

Since a low-voltage battery such as a mobile phone battery is used in a biomolecule detection device according to the present invention, an area of a buffer filling part which is under the influence of an electric field in the biomolecule detection device must be minimized. Thus, the buffer filling part may be in the form of a capillary microchannel or a thin plate. Although the buffer filling part can be filled with only a buffer, it may also be packed with a homogeneous gel matrix such as agarose, polyacrylamide, or silica, in order to increase a contact time of a sample with a probe biomolecule.

An electrophoresis unit of the biomolecule detection chip 21 includes two substrates 2116 and 2117 facing each other. An electrophoretic gel 2112 and first, second, and third antibodies 2113, 2114, and 2115 are interposed between the two substrates 2116 and 2117. The substrates 2116 and 2117 may be made of a transparent material to allow visible/UV light to be transmitted therethrough. The number of types of antibodies is not particularly limited and may be variously determined according to the purpose of detection.

In order to measure the quantity of light in each antibody region, photodiodes 2121 are broadly arranged under the substrate 2117 to form a photodiode array 212, and thus, the photodiode array 212 has an area corresponding to the total area of the electrophoretic gel 2112 including all the antibody regions. A lead-out circuit (not shown) for measuring the voltage distribution along the photodiode array 212 is disposed around the photodiode array 212.

Figure 3:
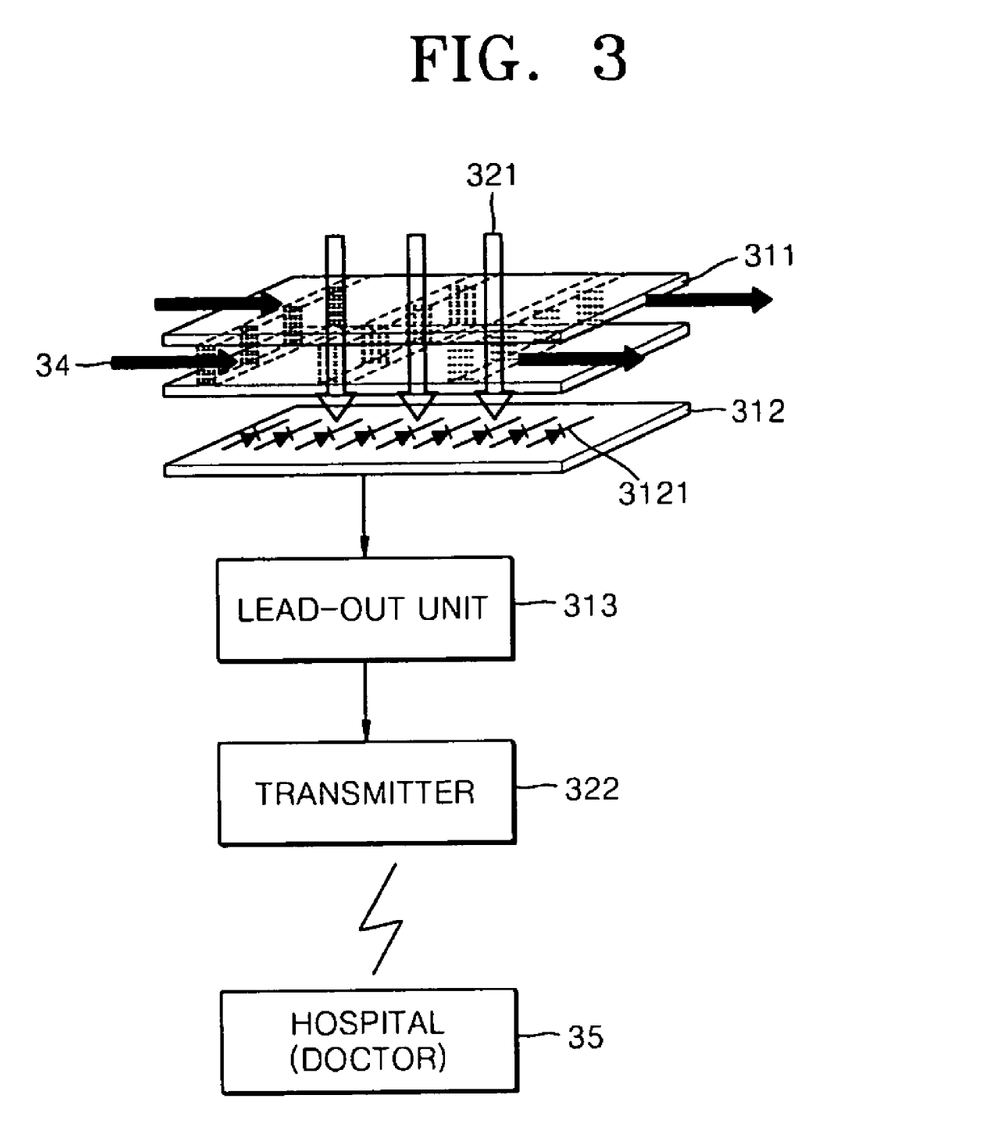
FIG. 3 is a schematic view illustrating the conversion of biomolecule detection results obtained using light to electrical signals and the wireless transmission of the electrical signals.

FIG. 3 is a schematic view illustrating the conversion of biomolecule detection results obtained using light to electrical signals and the wireless transmission of the electrical signals.

Referring to FIG. 3, in order to determine if a target biomolecule is present in a sample, the sample is mixed with a solution including a molecule capable of binding with the target biomolecule and absorbing light emitted from an optical source or a molecule capable of binding with the target biomolecule, absorbing light emitted from the optical source, and emitting light with a predetermined wavelength, and the resultant sample solution 34 is loaded on a filter (not shown) of an electrophoresis unit 311. The filter may be a top portion of a gel on which the sample solution 34 is loaded, or alternatively, a device which is separately disposed on top of the gel for separating blood cells. In the present invention, it is possible to prevent blood cells from entering into a gel by adjusting the pore size of the gel. Thus, there is no need to separately perform the separation of blood cells from blood.

After the sample solution 34 loaded on the gel passes through the last antibody region, a cover of a mobile phone is closed, and then, light 321, e.g., white light emitted from LCD or UV light emitted from a UV source disposed at the cover of the mobile phone is irradiated to the electrophoresis unit 311. At this time, antigen-antibody interaction may occur in each antibody region. If a predetermined antigen is absent in a sample, antigen-antibody interaction may not occur in a predetermined antibody region. In the present invention, in order to attach a side-chain molecule capable of absorbing visible/UV light to an antigen protein in blood, a mixture of a protein dye, gold particles, or a fluorophore reagent with initial blood is loaded on a gel.

The quantity of light that passes through each antibody region is changed according to the degree of antigen-antibody interaction. Thus, the amount of current flowing in photodiodes 3121 of a photodiode array 312 disposed under the electrophoresis unit 311 is changed. The amount of current is read as a voltage distribution by a lead-out unit 313 disposed around the photodiode array 312. The voltage values are transmitted to a terminal 35 of a (hospital) doctor via a transmitter 322. The doctor can analyze the received data and then feedback the doctor's observations and diagnosis to an individual.

Figure 4:
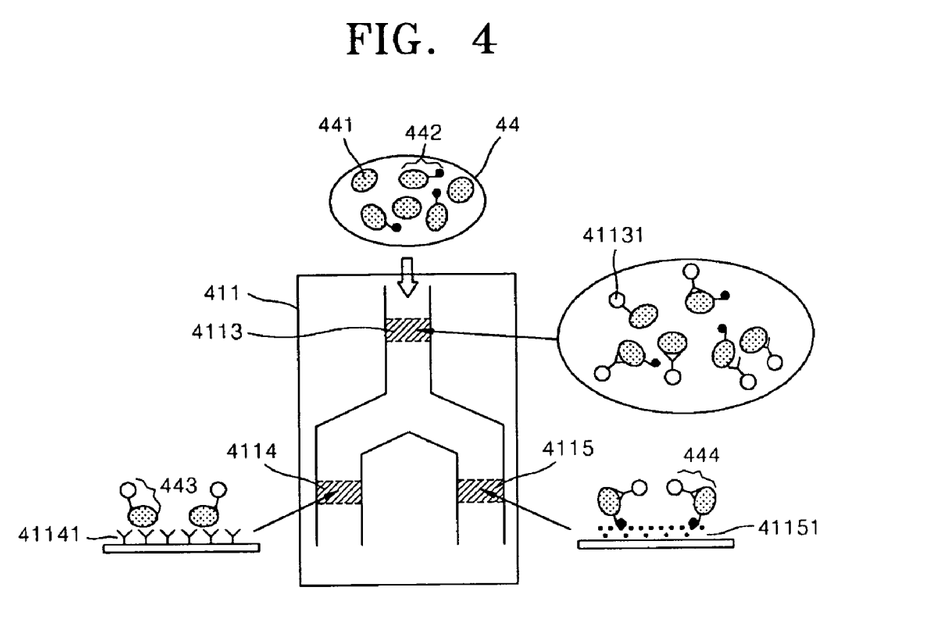
FIG. 4 is a schematic view illustrating a process of detecting liver cancer using a biomolecule detection device according to the present invention.

FIG. 4 is a schematic view illustrating a process of detecting liver cancer using a biomolecule detection device according to the present invention.

Alphafetoprotein (AFP) is a protein found in liver cancer patients. AFP is also expressed in normal persons suffering from inflammations. Meanwhile, the addition of fucose to AFT by post translational modification generates AFP-L3. AFP-L3 is known as a liver cancer marker protein that is significantly detected in patients suffering from liver cancer.

Referring to FIG. 4, an electrophoresis unit 411 includes a microchannel which includes an AFP-detecting antibody region 4113 including an AFP-detecting antibody 41131. The microchannel is branched into two sub-microchannels respectively including an anti-AFP antibody immobilization region 4114 immobilized with an AFP-binding antibody 41141 and an anti-AFP-L3 antibody immobilization region 4115 immobilized with an AFP-L3-binding antibody 41151. The AFP-detecting antibody 41131 can bind with an antigen labeled with a protein-attachable dye such as fluorophore or gold colloid. The protein-attachable dye promotes AFP detection by absorbing visible/UV light. The AFP-L3-binding antibody 41151 may be fucose-reactive lectin.

When a sample 44 containing an AFP 441 and an AFP-L3 442 is loaded in the microchannel, the AFP 441 and the AFP-L3 442 are bound to the AFP-detecting antibody 41131, and two equal volumes of the sample solution containing an AFP-AFP-detecting antibody complex 443 and an AFP-L3-AFP-detecting antibody complex 444 are respectively allowed to pass through the two sub-microchannels. In the two sub-microchannels, the AFP-AFP-detecting antibody complex 443 and the AFP-L3-AFP-detecting antibody complex 444 are respectively bound to the AFP-binding antibody 41141 and the AFP-L3-binding antibody 41151. The strengths of signals generated from the two sub-microchannels are analyzed for the detection of liver cancer.

Figure 5:
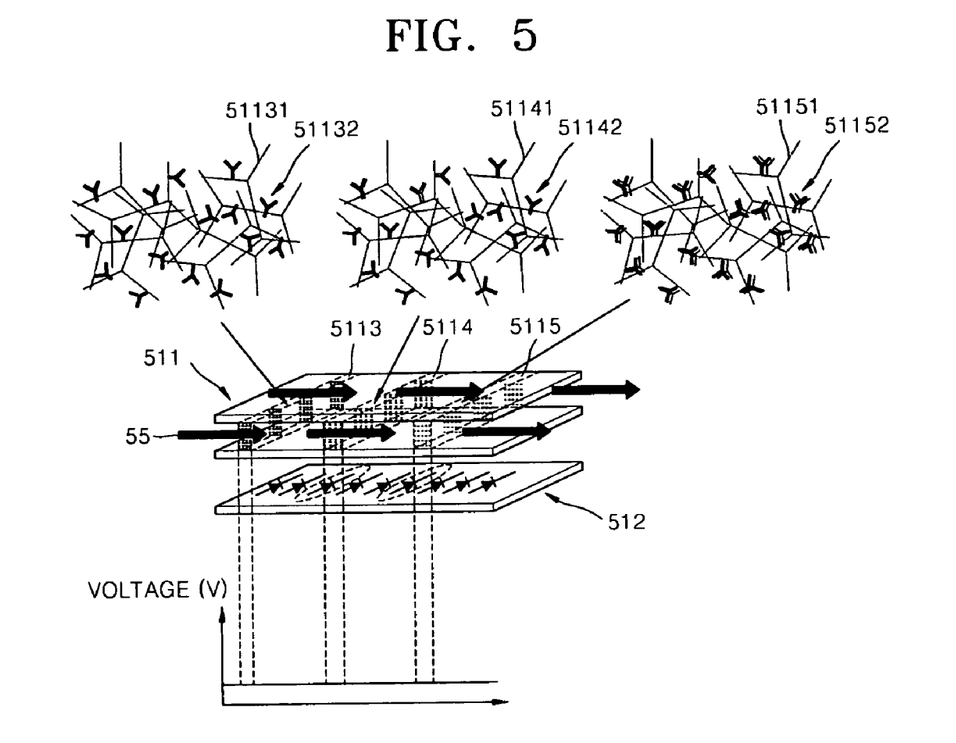
FIG. 5 illustrates a photodiode array-detected voltage in a case where a target biomolecule is absent in a sample.

FIG. 5 illustrates a photodiode array-detected voltage in a case where a target biomolecule is absent in a sample.

Referring to FIG. 5, an electrophoresis unit 511 includes a first antibody immobilization region 5113, a second antibody immobilization region 5114, and a third antibody immobilization region 5115. The first antibody immobilization region 5113 includes a gel in which a first antibody 51132 is immobilized in a microstructural network of glass fiber or polymer 51131. A second antibody 51142 and a third antibody 51152 are respectively immobilized in the second antibody immobilization region 5114 and the third antibody immobilization region 5115 in the same manner as above. A sample solution 55 obtained by mixing a sample with a predetermined molecule capable of binding with a predetermined antigen and absorbing visible/UV light is loaded in the electrophoresis unit 511.

While the sample solution 55 passes through the electrophoresis unit 511, macromolecules (e.g., blood cells) are filtered out through a filter (not shown). In the first antibody immobilization region 5113, an antigen (i.e., a first antigen) capable of undergoing an antigen-antibody interaction with the first antibody 51132 is bound to the first antibody 51132, and the remaining sample solution migrates by electrophoresis toward the second antibody region 5114. In the second antibody region 5114, an antigen (i.e., a second antigen) capable of undergoing an antigen-antibody interaction with the second antibody 51142 is bound to the second antibody 51142, and the remaining sample solution migrates by electrophoresis toward the third antibody region 5115. The same electrophoresis as above is performed in the third antibody region 5115.

Meanwhile, an antigen used as a marker protein capable of binding with an antibody may be absent in an initial sample. In this case, an antigen-antibody interaction does not occur. In the present invention, a marker protein in an initial sample is linked with a molecule capable of absorbing visible/UV light. Thus, if an antigen-antibody interaction event has occurred in an antibody immobilization region, light absorption by the molecule will occur in the antibody immobilization region.

As shown in FIG. 5, if marker proteins capable of binding with antibodies are absent in an initial sample, photodiodes disposed below the antibodies will mostly absorb incident visible/UV light, except visible/UV light absorbed by glass fiber or polymer components. FIG. 5 illustrates a voltage distribution in a case where marker proteins for the first, second, and third antibodies 51132, 51142, and 51152 are absent in the sample 55.

Figure 6:
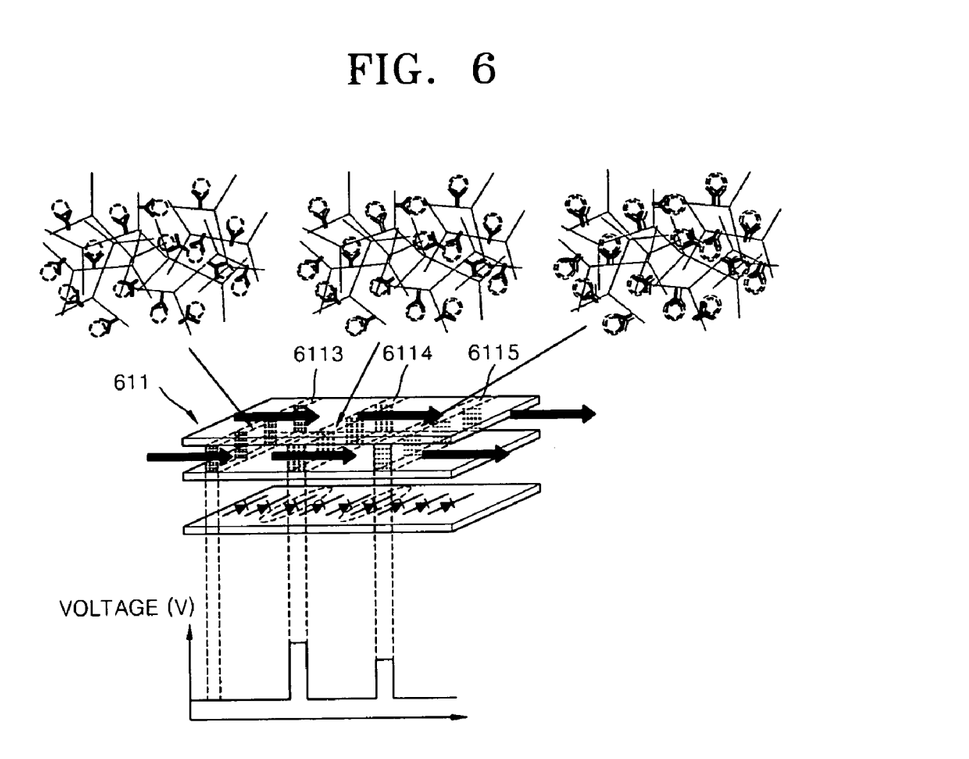
FIG. 6 illustrates a photodiode array-detected voltage in a case where a target biomolecule is present in a sample.

FIG. 6 illustrates a photodiode array-detected voltage in a case where a target biomolecule is present in a sample.

Referring to FIG. 6, an electrophoresis unit 611 has the same structure as the electrophoresis unit illustrated in FIG. 5. If a biomarker protein in a sample reacts with an antibody, absorption of visible/UV light directly proportional to the number of the biomarker protein molecules will occur.

FIG. 6 illustrates that no antigen-antibody interaction has occurred in a first antibody region 6113, much interaction has occurred between antigens and antibodies in a second antibody region 6114, and less interaction has occurred between antigens and antibodies in a third antibody region 6115. Thus, zero voltage is measured in the first antibody region 6113, a higher voltage is measured in the second antibody region 6114, and a lower voltage is measured in the third antibody region 6115. That is, FIG. 6 illustrates that marker proteins (antigens) for second and third antibodies are present in a sample.

With respect to the voltage measurement principle, when a marker protein linked with a molecule capable of absorbing visible/UV light emitted from an optical source is bound to an antibody specific to the marker protein, absorption of visible/UV light directly proportional to the number of the marker protein molecules occurs, thereby reducing the number of photons reaching the underlying photodiodes.

If the number of photons is reduced, the amount of current flowing between two electrodes in each photodiode is reduced, thereby increasing a voltage across the two electrodes.

Figure 7:
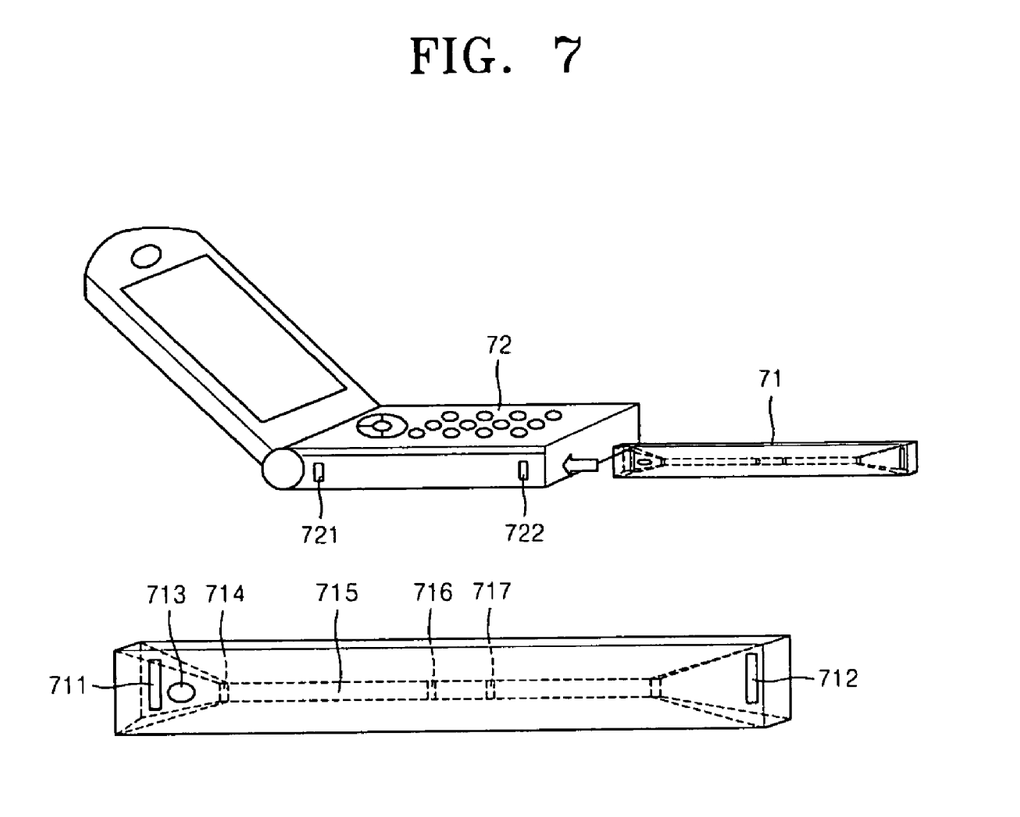
FIG. 7 is a view illustrating a biomolecule detection device according to another embodiment of the present invention and a mobile phone for biomolecule detection including the device.

FIG. 7 is a view illustrating a biomolecule detection device according to another embodiment of the present invention and a mobile phone for biomolecule detection including the device.

Referring to FIG. 7, the width and thickness of a biomolecule detection device 71 are similar to those of a mobile phone body 72. The biomolecule detection device 71 is attached to a side of the mobile phone body 72, and includes electrodes 711 and 712, a sample inlet 713, a filter 714, and a microchannel 715. A control antibody region 716 and a capturing antibody region 717 are disposed in the microchannel 715. The sample inlet 713 is usually plugged to prevent internal contamination of the biomolecule detection device 71. In a case where the biomolecule detection device 71 contains a matrix such as a gel, the sample inlet 713 serves to prevent the evaporation of internal moisture. The electrodes 711 and 712 are respectively matched to electrodes 721 and 722 disposed at the side of the mobile phone body 72.

Figure 8:
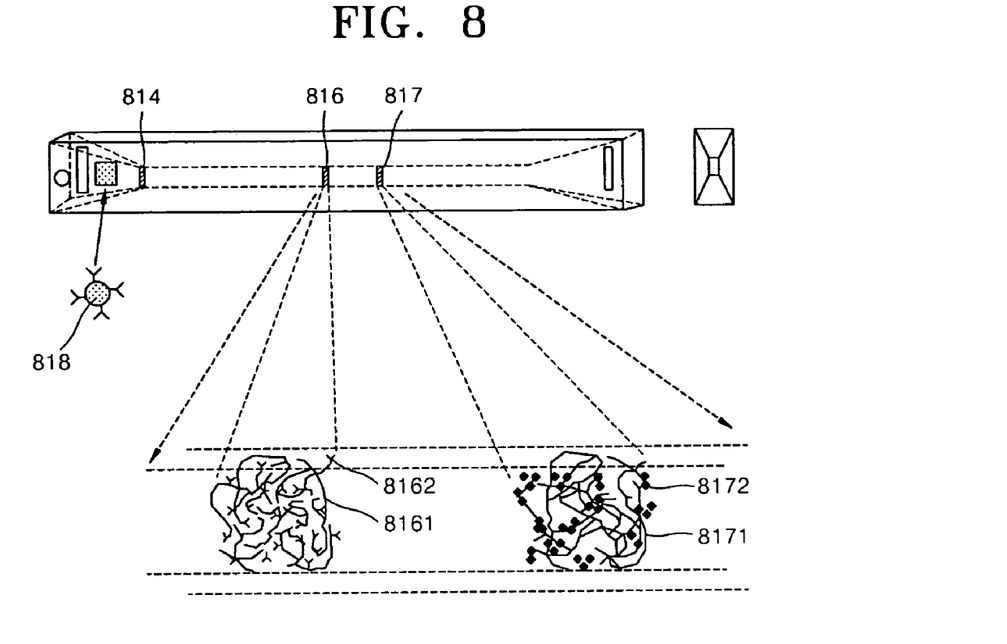
FIG. 8 is a detailed view of an electrophoresis unit of the biomolecule detection device illustrated in FIG. 7.

FIG. 8 is a detailed view of an electrophoresis unit of the biomolecule detection device illustrated in FIG. 7.

Referring to FIG. 8, a detecting antibody 818 conjugated with a gold colloid is patched around a sample inlet 814. When a sample is loaded, the detecting antibody 818 is dissolved by moisture contained in the sample and then reacts with a target biomolecule in the sample. A control antibody 8162 and a capturing antibody 8172 may be directly immobilized on the bottom of a channel. However, it is preferred that the control antibody 8162 and the capturing antibody 8172 are immobilized on polymer materials 8161 and 8171 such as glass fibers or polysaccharides. Therefore, antibody immobilization efficiency can be increased, thereby increasing detection sensitivity.

In the case of using a gold colloid, the presence of a target biomolecule can be visually detected by color change. In this case, there is no need to use photodiodes.

Figure 9:
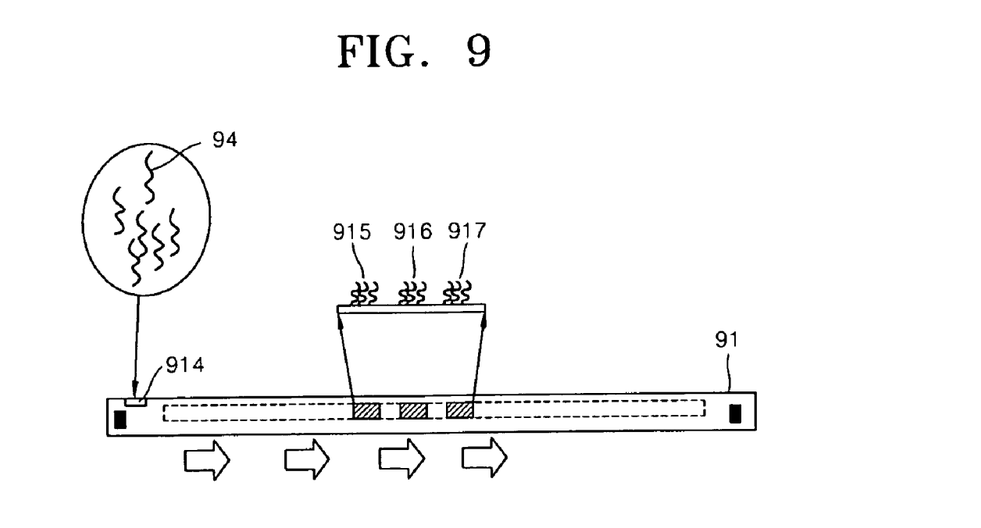
FIG. 9 is a view illustrating a biomolecule detection device according to still another embodiment of the present invention.

FIG. 9 is a view illustrating a biomolecule detection device according to still another embodiment of the present invention.

Referring to FIG. 9, a nucleic acid such as DNA or RNA is used as a biomolecule. A labeled target nucleic acid 94 is loaded into a sample inlet 914, and probe nucleic acids 915, 916, and 917 are immobilized in a biomolecule detection device 91. The biomolecule detection device 91 can be used for genotyping, gene identification, gene expression profiling, etc.

Data transmission can be achieved through a photodiode array (not shown) disposed below the probe nucleic acids 915, 916, and 917. When performing single-nucleotide polymorphism (SNP) analysis for probe nucleic acids with only a 1-bp difference, non-specific DNAs or chemical materials can also be used to induce more specific hybridization. For example, salmon sperm DNA or Ficoll can be used. The number of probe nucleic acids to be used can be determined according to the purpose of detection.

The present invention also provides a method of detecting a target biomolecule using a mobile phone for biomolecule detection according to the present invention. The target biomolecule detection method includes: loading a sample on an electrophoresis unit to perform electrophoresis; irradiating light to the electrophoresis unit using an optical source; and transmitting the detection results wirelessly.

The target biomolecule detection method may further include mixing the sample with a solution including a molecule capable of binding with the target biomolecule and absorbing light emitted from the optical source or a molecule capable of binding with the target biomolecule, absorbing light emitted from the optical source, and emitting light with a predetermined wavelength, prior to loading the sample on the electrophoresis unit.

The type of the sample is not particularly limited. For example, the sample may be selected from the group consisting of saliva, urine, blood, serum, cell culture, and drinking water.

While the present invention has been particularly shown and described with reference to exemplary embodiments thereof, it will be understood by those of ordinary skill in the art that various changes in form and details may be made therein without departing from the spirit and scope of the present invention as defined by the following claims.

As described above, a biomolecule detection device according to the present inventiona can be used for biomolecule detection (e.g., self-diagnosis of disease) regardless of time and place. A mobile phone for biomolecule detection according to the present invention can be used for biomolecule detection (e.g., self-diagnosis of disease) regardless of time and place, and at the same time, can transmit the detection results to a medically trained person (e.g., a doctor) and receive the medical consultation wirelessly. A biomolecule detection method according to the present invention can be used to perform biomolecule detection (e.g., self-diagnosis of disease) regardless of time and place, and transmit the detection results to a medically trained person (e.g., a doctor) and receive the medical consultation wirelessly.

What is claimed is:

1. A portable handheld wireless device for biomolecule detection comprising:
   an electrophoresis unit comprising:
      a sample inlet;
      a filter in fluid communications with the sample inlet;
      an electrophoretic gel in fluid communications with the filter;
      a plurality of immobilization regions serially spaced apart from one another along a separation pathway within the electrophoretic gel; and
      opposing electrodes for providing an electric field that defines the separation pathway through the electrophesis gel unit and through the immobilization regions;
   an optical source irradiating light to the electrophoresis unit, wherein the electrophoresis unit is sized, shaped, and arranged on the portable handheld wireless device so as to receive light irradiating from a screen of the portable handheld wireless device during operation;
   a conversion unit comprising a plurality of detectors optically aligned with corresponding immobilization regions in the electrophoretic gel in which the optically aligned detectors are configured to physically respond to changes in light that transmits through the immobilization regions and strikes onto corresponding optically aligned detectors which in turn drives production of corresponding electrical signals; and
   a lead-out unit receiving, converting, and transmitting the electrical signals.

2. The portable handheld wireless device of claim 1, wherein each immobilization region comprises a glass fiber or a polymer material which is disposed in the electrophoretic gel and which has a probe biomolecule immobilized onto each immobilization region.

3. The portable handheld wireless device of claim 1, wherein the electrophoretic gel is an agarose gel or a polyacrylamide gel.

4. The portable handheld wireless device of claim 1 wherein the portable handheld wireless device comprises a mobile phone.

5. The portable handheld wireless device of claim 1, wherein the plurality of immobilization regions comprises a plurality of antibody immobilization regions.

6. The portable handheld wireless device of claim 5, wherein the plurality of immobilization regions comprises a first antibody immobilization region, a second antibody immobilization region, and a third antibody immobilization region.

7. The portable handheld wireless device of claim 6, wherein the first antibody immobilization region having a first antibody affixed onto the first antibody immobilization region, the second immobilization region having a second antibody affixed onto the second antibody immobilization region, and the third antibody immobilization region having a third antibody affixed onto the third antibody immobilization region.

8. The portable handheld wireless device of claim 1, wherein the immobilization regions comprise nucleic acid immobilization regions having a probe nucleic acid affixed onto the nucleic acid immobilization regions.

9. The portable handheld wireless device of claim 8, wherein the probe nucleic acid is selected from the group consisting of DNAs, RNAs, PNAs, LNAs, and hybrids thereof.

10. The portable handheld wireless device of claim 8, wherein the immobilization regions comprise protein immobilization regions having a probe protein affixed onto the protein acid immobilization regions such that the probe protein is selected from the group consisting of enzymes, substrates, antigens, antibodies, ligands, aptamers, and receptors.

11. The portable handheld wireless device of claim 1, wherein the electrophoresis unit further comprises two substrates facing each other, and having the electrophoretic gel and the immobilization regions interposed between the two substrates.

12. The portable handheld wireless device of claim 11, wherein the two substrates are transparent.

13. The portable handheld wireless device of claim 1, wherein the optically aligned detectors of the conversion unit are photodiodes.

14. The portable handheld wireless device of claim 13, wherein the photodiodes are capable of detecting visible light or UV light.

15. The portable handheld wireless device of claim 1, further comprising:
   a power supply unit supplying power to the electrophoresis unit, the conversion unit, and the lead-out unit;
   the optical source configured to irradiate light through the immobilization regions and onto the detectors of the electrophoresis unit; and
   a transmitter configured to transmit wirelessly information corresponding to the electrical signals received from the lead-out unit.

16. The portable handheld wireless device of claim 15, wherein the optical source is an LCD screen of a mobile phone.

17. The portable handheld wireless device of claim 15, wherein the optical source comprises a UV light source.

18. A method of detecting a target biomolecule comprising:
   obtaining a portable handheld wireless device for biomolecule detection comprising:
      an electrophoresis unit comprising:
         a sample inlet;
         a filter in fluid communications with the sample inlet;
         an electrophoretic gel in fluid communications with the filter;
         a plurality of immobilization regions serially spaced apart from one another and positioned along a separation pathway within the electrophoretic gel wherein the immobilization regions comprise a first, second and third immobilization regions; and
         opposing electrodes for providing an electric field that defines the separation pathway through the electrophoresis gel unit and through the immobilization regions;
      an optical source irradiating light to the electrophoresis unit, wherein the electrophoresis unit is sized, shaped, and arranged on the portable handheld wireless device so as to receive light irradiating from a screen of the portable handheld wireless device during operation;

a conversion unit comprising a plurality of detectors optically aligned with corresponding immobilization regions in the electrophoretic gel in which the optically aligned detectors are configured to physically respond to changes in light that transmits through the immobilization regions and strikes onto corresponding optically aligned detectors which in turn drives production of corresponding electrical signals;

a lead-out unit receiving, converting, and transmitting the electrical signals, a power supply unit supplying power to the electrophoresis unit, the conversion unit, and the lead-out unit;

an optical source configured to irradiate light through the immobilization regions and onto the detectors of the electrophoresis unit; and a transmitter configured to transmit wirelessly information corresponding to the electrical signals received from the lead-out unit; loading a sample into the sample inlet of the electrophoresis unit;

applying an electric field across the opposing electrodes to define the separation pathway through the electrophoresis gel unit and through the immobilization regions to promote separation of individual components of the sample along the separation pathway;

trapping and concentrating first, second and third target analytes at respective first, second and third immobilization regions when the electric field is applied across the opposing electrodes;

irradiating light from an optical source through the first, second, and third target immobilization regions when the first, second and third target analytes are respectively trapped and concentrated at the first, second and third immobilization regions;

detecting light through the first, second, and third immobilization regions when the first, second and third target analytes are trapped and concentrated at respective first, second and third immobilization regions by using the optically aligned detectors to respectively produce first, second and third electrical signals; and transmitting first, second, and third wireless signals corresponding to the respective first, second and third electrical signals.

19. The method of claim 18, further comprising receiving the first, second, and third wireless signals at a remote terminal.

20. The method of claim 18, wherein the sample is selected from the group consisting of saliva, urine, blood, serum, cell culture, and drinking water.

* * * * *